United States Patent
Hastings et al.

(10) Patent No.: US 8,060,184 B2
(45) Date of Patent: *Nov. 15, 2011

(54) METHOD OF NAVIGATING MEDICAL DEVICES IN THE PRESENCE OF RADIOPAQUE MATERIAL

(75) Inventors: Roger N. Hastings, Maple Grove, MN (US); Steven J. Ferry, Excelsior, MN (US); Demetrius K. Lopes, Chicago, IL (US)

(73) Assignee: Stereotaxis, Inc., St. Louis, MO (US)

( * ) Notice: Subject to any disclaimer, the term of this patent is extended or adjusted under 35 U.S.C. 154(b) by 921 days.

This patent is subject to a terminal disclaimer.

(21) Appl. No.: 11/781,236

(22) Filed: Jul. 20, 2007

(65) Prior Publication Data

US 2008/0077007 A1    Mar. 27, 2008

Related U.S. Application Data

(63) Continuation of application No. 10/186,264, filed on Jun. 28, 2002, now Pat. No. 7,248,914.

(51) Int. Cl.
*A61B 5/05* (2006.01)
(52) U.S. Cl. .................. 600/424; 606/130; 606/108
(58) Field of Classification Search ............ 600/407, 600/411, 420–424, 585; 606/130, 1, 108
See application file for complete search history.

(56) References Cited

U.S. PATENT DOCUMENTS

| | | | |
|---|---|---|---|
| 3,358,676 A | 12/1967 | Frei et al. .................. 600/12 |
| 4,173,228 A | 11/1979 | Van Steenwyk et al. | |
| 5,211,165 A * | 5/1993 | Dumoulin et al. .......... 600/410 |
| 5,558,091 A * | 9/1996 | Acker et al. .................. 600/424 |
| 5,654,864 A | 8/1997 | Ritter et al. | |
| 5,729,129 A * | 3/1998 | Acker .................. 324/207.12 |
| 5,868,674 A | 2/1999 | Glowinski et al. .......... 600/410 |
| 5,931,818 A | 8/1999 | Werp et al. | |
| 6,014,580 A | 1/2000 | Blume et al. | |
| 6,015,414 A | 1/2000 | Werp et al. | |
| 6,128,174 A | 10/2000 | Ritter et al. | |
| 6,148,823 A | 11/2000 | Hastings | |
| 6,152,933 A | 11/2000 | Werp et al. | |
| 6,157,853 A | 12/2000 | Blume et al. | |
| 6,165,193 A | 12/2000 | Greene et al. .................. 600/191 |
| 6,212,419 B1 | 4/2001 | Blume et al. | |
| 6,216,030 B1 | 4/2001 | Howard et al. .................. 600/427 |
| 6,241,671 B1 | 6/2001 | Ritter et al. | |
| 6,253,770 B1 | 7/2001 | Acker et al. .................. 128/899 |
| 6,272,370 B1 | 8/2001 | Gillies et al. .................. 600/411 |
| 6,292,678 B1 | 9/2001 | Hall et al. | |
| 6,296,604 B1 | 10/2001 | Garibaldi et al. | |
| 6,298,257 B1 | 10/2001 | Hall et al. | |
| 6,298,259 B1 | 10/2001 | Kucharczyk et al. .......... 600/411 |
| 6,304,768 B1 | 10/2001 | Blume et al. | |
| 6,304,769 B1 * | 10/2001 | Arenson et al. .................. 600/424 |
| 6,315,709 B1 | 11/2001 | Garibaldi et al. | |

(Continued)

*Primary Examiner* — Sanjay Cattungal
(74) *Attorney, Agent, or Firm* — Harness, Dickey & Pierce, P.L.C.

(57) ABSTRACT

A method of navigating the distal end of a medical device through an operating region in a subject's body includes displaying an x-ray image of the operating region, including the distal end of the medical device; determining the location of the distal end of the medical device in a reference frame translatable to the displayed x-ray image; and displaying an enhanced indication of the distal end of the medical device on the x-ray image to facilitate the navigation of the distal end of the device in the operating region.

11 Claims, 5 Drawing Sheets

U.S. PATENT DOCUMENTS

| | | | |
|---|---|---|---|
| 6,330,467 B1 | 12/2001 | Creighton, IV et al. | |
| 6,352,363 B1 | 3/2002 | Munger et al. | |
| 6,364,823 B1 | 4/2002 | Garibaldi et al. | |
| 6,375,606 B1 | 4/2002 | Garibaldi et al. | |
| 6,385,472 B1 | 5/2002 | Hall et al. | |
| 6,401,723 B1 | 6/2002 | Garibaldi et al. | |
| 6,428,551 B1 | 8/2002 | Hall et al. | |
| 6,459,924 B1 | 10/2002 | Creighton, IV et al. | |
| 6,475,223 B1 | 11/2002 | Werp et al. | |
| 6,505,062 B1 | 1/2003 | Ritter et al. | |
| 6,507,751 B2 | 1/2003 | Blume et al. | |
| 6,522,909 B1 | 2/2003 | Garibaldi et al. | |
| 6,524,303 B1 | 2/2003 | Garibaldi | |
| 6,527,782 B2 | 3/2003 | Hogg et al. | |
| 6,537,196 B1 | 3/2003 | Creighton, IV et al. | |
| 6,542,766 B2 | 4/2003 | Hall et al. | |
| 6,562,019 B1 | 5/2003 | Sell | |
| 6,626,902 B1 * | 9/2003 | Kucharczyk et al. | 606/41 |
| 6,630,879 B1 | 10/2003 | Creighton, IV et al. | |
| 6,662,034 B2 | 12/2003 | Segner et al. | |
| 6,677,752 B1 | 1/2004 | Creighton, IV et al. | |
| 6,702,804 B1 | 3/2004 | Ritter et al. | |
| 6,733,511 B2 | 5/2004 | Hall et al. | |
| 6,755,816 B2 | 6/2004 | Ritter et al. | |
| 6,817,364 B2 | 11/2004 | Garibaldi et al. | |
| 6,827,723 B2 | 12/2004 | Carson | 606/130 |
| 6,834,201 B2 * | 12/2004 | Gillies et al. | 600/411 |
| 6,902,528 B1 * | 6/2005 | Garibaldi et al. | 600/118 |
| 6,911,026 B1 | 6/2005 | Hall et al. | |
| 6,940,379 B2 | 9/2005 | Creighton | |
| 6,968,846 B2 | 11/2005 | Viswanathan | |
| 6,975,197 B2 | 12/2005 | Creighton, IV | |
| 6,980,843 B2 | 12/2005 | Eng et al. | |
| 7,008,418 B2 | 3/2006 | Hall et al. | |
| 7,010,338 B2 | 3/2006 | Ritter et al. | |
| 7,019,610 B2 | 3/2006 | Creighton, IV et al. | |
| 7,020,512 B2 | 3/2006 | Ritter et al. | |
| 7,048,716 B1 * | 5/2006 | Kucharczyk et al. | 604/164.01 |
| 7,066,924 B1 | 6/2006 | Garibaldi et al. | |
| 7,137,976 B2 | 11/2006 | Ritter et al. | |
| 7,161,453 B2 | 1/2007 | Creighton, IV | |
| 7,189,198 B2 | 3/2007 | Harburn et al. | |
| 7,190,819 B2 | 3/2007 | Viswanathan | |
| 7,211,082 B2 | 5/2007 | Hall et al | |
| 7,248,914 B2 * | 7/2007 | Hastings et al. | 600/424 |
| 7,264,584 B2 | 9/2007 | Ritter et al. | |
| 7,477,763 B2 * | 1/2009 | Willis et al. | 382/128 |
| 2001/0038683 A1 | 11/2001 | Ritter et al. | |
| 2002/0019644 A1 | 2/2002 | Hastings et al. | |
| 2002/0100486 A1 | 8/2002 | Creighton, IV et al. | |
| 2002/0177789 A1 | 11/2002 | Ferry et al. | |
| 2003/0125752 A1 | 7/2003 | Werp et al. | |
| 2003/0231789 A1 * | 12/2003 | Willis et al. | 382/128 |
| 2004/0006301 A1 | 1/2004 | Sell et al. | |
| 2004/0019447 A1 | 1/2004 | Shachar | |
| 2004/0030244 A1 | 2/2004 | Garibaldi et al. | |
| 2004/0064153 A1 | 4/2004 | Creighton, IV et al. | |
| 2004/0068173 A1 | 4/2004 | Viswanathan | |
| 2004/0133130 A1 | 7/2004 | Ferry et al. | |
| 2004/0147829 A1 | 7/2004 | Segner et al. | |
| 2004/0157082 A1 | 8/2004 | Ritter et al. | |
| 2004/0158972 A1 | 8/2004 | Creighton, IV et al. | |
| 2004/0186376 A1 | 9/2004 | Hogg et al. | |
| 2004/0249262 A1 | 12/2004 | Werp et al. | |
| 2004/0249263 A1 | 12/2004 | Creighton, IV | |
| 2004/0260172 A1 | 12/2004 | Ritter et al. | |
| 2004/0267106 A1 | 12/2004 | Segner et al. | |
| 2005/0004585 A1 | 1/2005 | Hall et al. | |
| 2005/0020911 A1 | 1/2005 | Viswanathan et al. | |
| 2005/0021063 A1 | 1/2005 | Hall et al. | |
| 2005/0033162 A1 | 2/2005 | Garibaldi et al. | |
| 2005/0043611 A1 | 2/2005 | Sabo et al. | |
| 2005/0065435 A1 | 3/2005 | Rauch et al. | |
| 2005/0096589 A1 | 5/2005 | Shachar | |
| 2005/0113628 A1 | 5/2005 | Creighton, IV et al. | |
| 2005/0113812 A1 | 5/2005 | Viswanathan et al. | |
| 2005/0113846 A1 | 5/2005 | Carson | 606/130 |
| 2005/0119556 A1 * | 6/2005 | Gillies et al. | 600/410 |
| 2005/0119687 A1 | 6/2005 | Dacey, Jr. et al. | |
| 2005/0182315 A1 | 8/2005 | Ritter et al. | |
| 2005/0256398 A1 | 11/2005 | Hastings et al. | |
| 2005/0273130 A1 | 12/2005 | Sell | |
| 2006/0004382 A1 | 1/2006 | Hogg et al. | |
| 2006/0009735 A1 | 1/2006 | Viswanathan et al. | |
| 2006/0025676 A1 | 2/2006 | Viswanathan et al. | |
| 2006/0025679 A1 | 2/2006 | Viswanathan et al. | |
| 2006/0025719 A1 | 2/2006 | Viswanathan et al. | |
| 2006/0036125 A1 | 2/2006 | Viswanathan et al. | |
| 2006/0036163 A1 | 2/2006 | Viswanathan | |
| 2006/0036213 A1 | 2/2006 | Viswanathan et al. | |
| 2006/0041178 A1 | 2/2006 | Viswanathan et al. | |
| 2006/0041179 A1 | 2/2006 | Viswanathan et al. | |
| 2006/0041180 A1 | 2/2006 | Viswanathan et al. | |
| 2006/0041181 A1 | 2/2006 | Viswanathan et al. | |
| 2006/0041245 A1 | 2/2006 | Ferry et al. | |
| 2006/0058646 A1 | 3/2006 | Viswanathan | |
| 2006/0061445 A1 | 3/2006 | Creighton, IV et al. | |
| 2006/0074297 A1 | 4/2006 | Viswanathan | |
| 2006/0079745 A1 | 4/2006 | Viswanathan | |
| 2006/0079812 A1 | 4/2006 | Viswanathan | |
| 2006/0094956 A1 | 5/2006 | Viswanathan | |
| 2006/0100505 A1 | 5/2006 | Viswanathan | |
| 2006/0114088 A1 | 6/2006 | Shachar | |
| 2006/0116633 A1 | 6/2006 | Shachar | |
| 2006/0144407 A1 | 7/2006 | Aliberto et al. | |
| 2006/0144408 A1 | 7/2006 | Ferry | |
| 2006/0145799 A1 | 7/2006 | Creighton, IV | |
| 2006/0270915 A1 | 11/2006 | Ritter et al. | |
| 2006/0270948 A1 | 11/2006 | Viswanathan et al. | |
| 2006/0278248 A1 | 12/2006 | Viswanathan | |
| 2007/0016010 A1 | 1/2007 | Creighton, IV et al. | |
| 2007/0016131 A1 | 1/2007 | Munger et al. | |
| 2007/0019330 A1 | 1/2007 | Wolfersberger | |
| 2007/0021731 A1 | 1/2007 | Garibaldi et al. | |
| 2007/0021742 A1 | 1/2007 | Viswanathan | |
| 2007/0021744 A1 | 1/2007 | Creighton, IV | |
| 2007/0030958 A1 | 2/2007 | Munger | |
| 2007/0032746 A1 | 2/2007 | Sell | |
| 2007/0038064 A1 | 2/2007 | Creighton, IV | |
| 2007/0038065 A1 | 2/2007 | Creighton, IV et al. | |
| 2007/0038074 A1 | 2/2007 | Ritter et al. | |
| 2007/0038410 A1 | 2/2007 | Tunay | |
| 2007/0040670 A1 | 2/2007 | Viswanathan | |
| 2007/0043455 A1 | 2/2007 | Viswanathan et al. | |
| 2007/0049909 A1 | 3/2007 | Munger | |
| 2007/0055124 A1 | 3/2007 | Viswanathan et al. | |
| 2007/0055130 A1 | 3/2007 | Creighton, IV | |
| 2007/0060829 A1 | 3/2007 | Pappone | |
| 2007/0060916 A1 | 3/2007 | Pappone | |
| 2007/0060962 A1 | 3/2007 | Pappone | |
| 2007/0060966 A1 | 3/2007 | Pappone | |
| 2007/0060992 A1 | 3/2007 | Pappone | |
| 2007/0062546 A1 | 3/2007 | Viswanathan et al. | |
| 2007/0062547 A1 | 3/2007 | Pappone | |
| 2007/0073288 A1 | 3/2007 | Hall et al. | |
| 2007/0088197 A1 | 4/2007 | Garibaldi et al. | |
| 2007/0135804 A1 | 6/2007 | Ritter | |
| 2007/0137656 A1 | 6/2007 | Viswanathan | |
| 2007/0146106 A1 | 6/2007 | Creighton, IV | |
| 2007/0149946 A1 | 6/2007 | Viswanathan | |
| 2007/0161882 A1 | 7/2007 | Pappone | |
| 2007/0167720 A1 | 7/2007 | Viswanathan | |
| 2007/0179492 A1 | 8/2007 | Pappone | |
| 2007/0197899 A1 | 8/2007 | Ritter et al. | |
| 2007/0197901 A1 | 8/2007 | Viswanathan | |
| 2007/0197906 A1 | 8/2007 | Ritter | |
| 2007/0225589 A1 | 9/2007 | Viswanathan | |

\* cited by examiner

METHOD OF NAVIGATING MEDICAL DEVICES IN THE PRESENCE OF RADIOPAQUE MATERIAL

This application is a continuation of U.S. patent application Ser. No. 10/186,264, filed Jun. 28, 2002, now U.S. Pat. No. 7,248,914, entitled "Method of Navigating Medical Devices In The Presence Of Radiopaque Material", of which is incorporated herein by reference.

FIELD OF THE INVENTION

This invention relates to the navigation of medical devices in the presence of radiopaque materials, and in particular to a method of navigating a medical device for the delivery of radiopaque materials.

BACKGROUND OF THE INVENTION

The navigation of the distal end of a medical device through the body, whether by conventional mechanical means or magnetic means, is usually facilitated by x-ray imaging of the operating region. However, when there is radiopaque material in the operating region, it is often difficult to discern the distal end of the medical device. This occurs, for example when the medical device is delivering a radiopaque material, such as a radiopaque embolic material, or a radiopaque embolization coil. The presence of these materials in the medical device or in the operating region can make it difficult for the physician to "see" the distal end of the medical device on x-ray images, and thus make it difficult to quickly and accurately navigate the distal end of the medical device.

SUMMARY OF THE INVENTION

Broadly, the method of this invention relates the to navigation of medical devices in a subject's body. The method broadly comprises displaying an x-ray image of the operating region, including the distal end of the medical device; determining the location of the distal end of the medical device in a reference frame translatable to the displayed x-ray image; and displaying an enhanced indication of the distal end of the medical device on the x-ray image to facilitate the navigation of the distal end of the device in the operating region. The method of this invention allows a physician to more accurately track the position of the distal end of the medical device during navigation, this facilitates navigation, and particularly the accurate delivery of radiopaque materials in a subject's body.

DETAILED DESCRIPTION OF THE INVENTION

Figure 1:
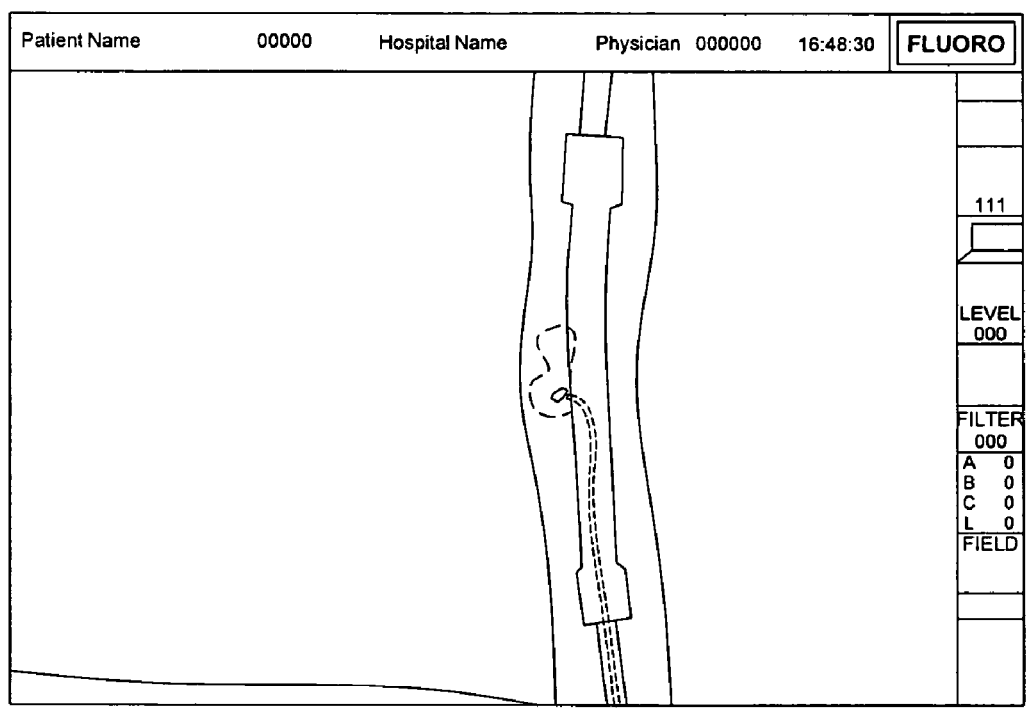
FIG. 1 is a radiograph an aneurysm phantom showing a medical device navigated to the mouth of the aneurysm.
Figure 2A:
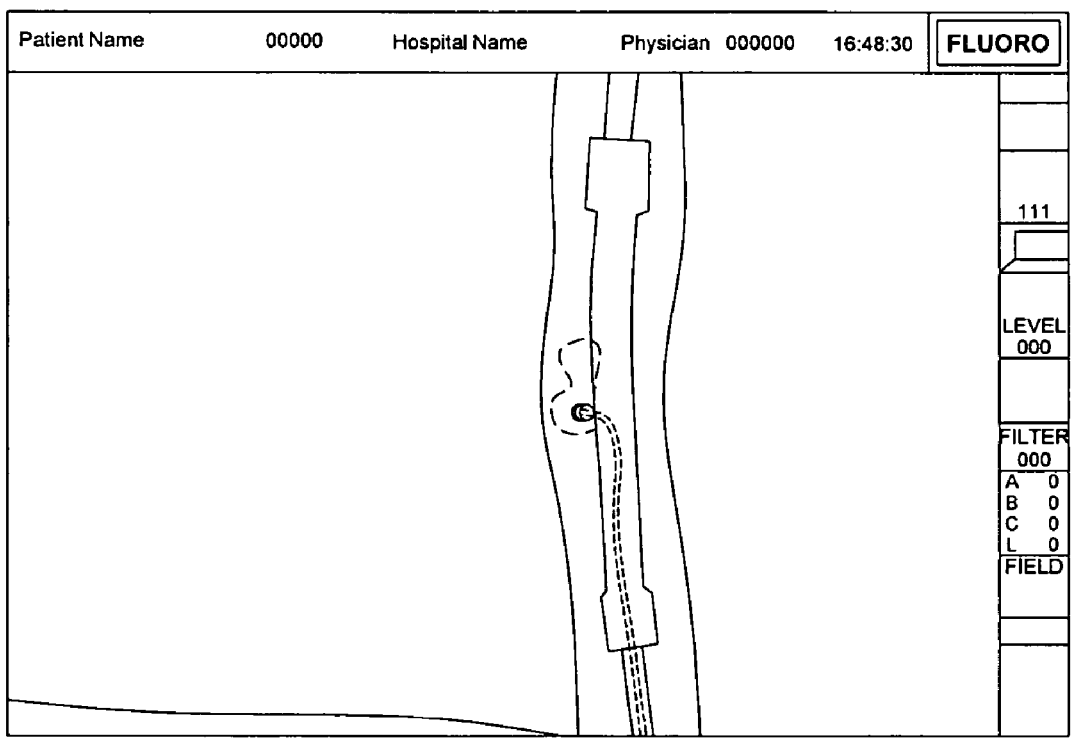
FIG. 2a is a radiograph of an aneurysm phantom and catheter after radiopaque coils have been released into the aneurysm body.
Figure 2B:
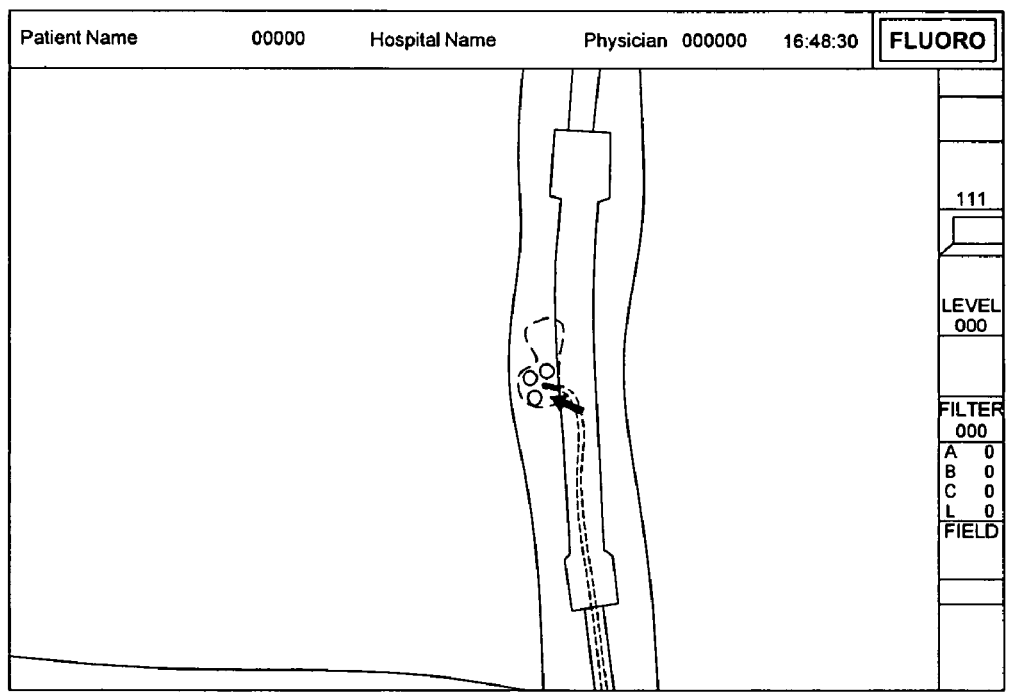
FIG. 2b is a radiograph show in FIG. 2a with an line indicating the distal end of the medical device and an arrow indicating the distal end of the medical device, in accordance with the principles of this invention.

The present invention relates to a method of navigating the distal end of a medical device through an operating region in a subject's body. Broadly, this method comprises displaying an x-ray or other image of the operating region, including the distal end of the medical device, for example as shown in FIG. 1. The location of the distal end of the medical device is then determined in a reference frame translatable to the displayed x-ray image. Based upon the determined location, an enhanced indication of the distal end of the medical device is then displayed on the x-ray image to facilitate the navigation of the distal end of the device in the operating region. This is shown in FIG. 2. This helps the user identify the location of the distal end of the medical device, to facilitate navigating the device.

This method can be used with any type of medical device, such as a catheter, endoscope, guide wire, sampling (e.g. biopsy) device, drug or device delivery catheter, sensing device, or pacing device, etc. The method can be employed with conventional navigation, i.e. devices with preformed tips for manipulation in the body, or devices with pull or push wires for directing the distal tip of the medical device. The method can also be employed with non-conventional navigation modes such as magnetic navigation, (e.g. the application of an external magnetic field to orient the distal tip) or the use of magnetostrictive or electrostrictive devices to direct the distal tip of the medical device.

While described herein in terms of x-ray imaging and interference from radio opaque materials, this invention also applies to other imaging modalities where there is material present which interferes with the accurate imaging and display of the distal end of the medical device. In such cases, the distal tip can still be localized, and the position indicated independent of the local interference.

Figure 3:
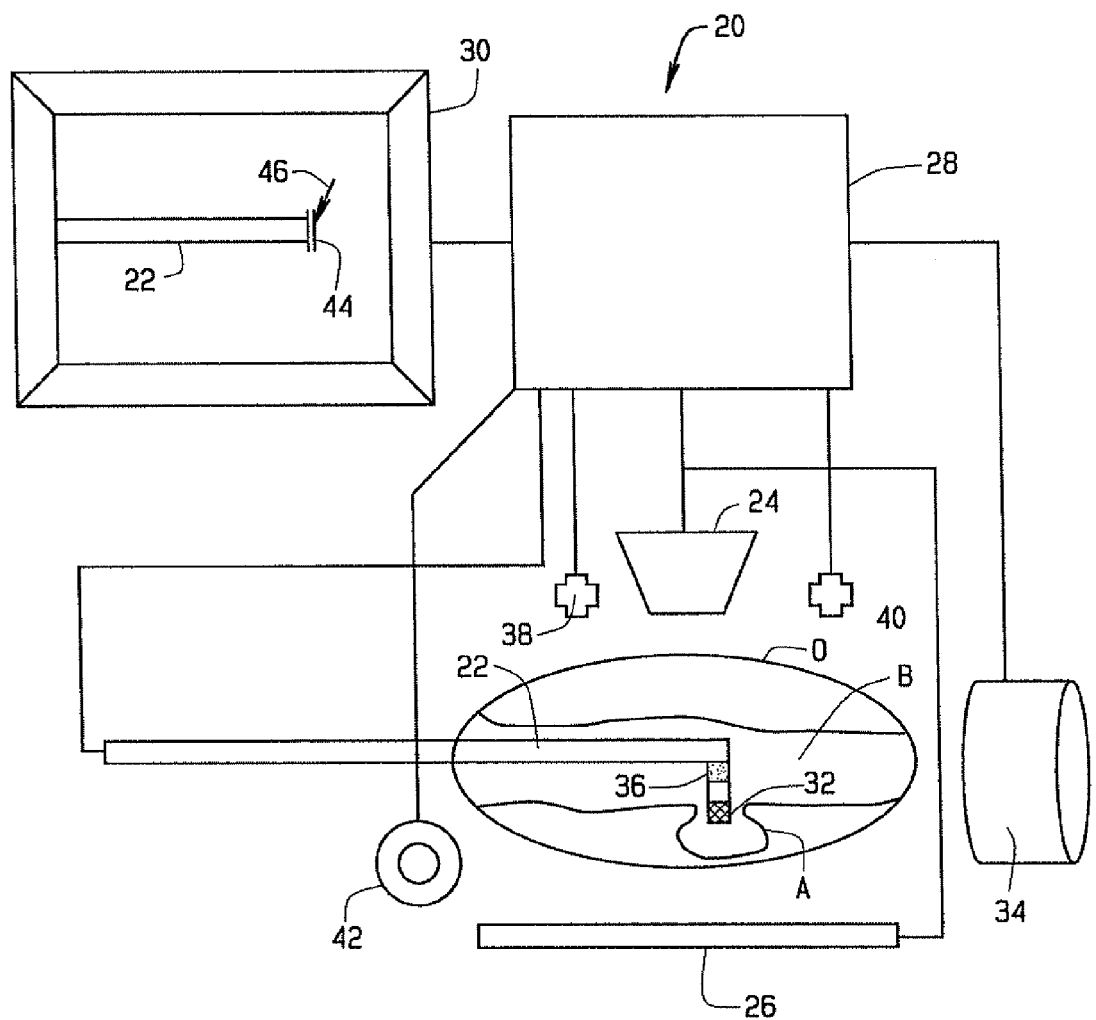
FIG. 3 is a schematic diagram of a system for carrying out the method of the present invention.

As shown schematically in FIG. 3 a system for implementing the method of this invention is indicated generally as 20. The system 20 comprises a catheter 22 for example, for delivering radio opaque coils to a vascular defect such as an aneurysm A in blood vessel B in the operating region O of the subject. In this preferred embodiment, there is an imaging system comprising an x-ray source 24 and a solid state imaging plate 26 connected through a processor 28 to a display 30. The catheter 22 has a magnetically responsive element 32 so that the distal end of the catheter 22 can be controlled by a external magnet system represented schematically at 34. The embolic substance or embolizing coils used to fill the aneurysm A are typically radiopaque so that they can be seen in x-ray imaging. However, this radiopacity can make it hard to distinguish the distal end of the catheter 22. As shown in FIG. 3, the catheter 22 can include a coil 36 for receiving signals from transmitters 38 and 40 at known fixed locations, in order to determine the position and orientation of the distal end of the catheter 22 in which the coil 36 is located. (Alternatively, the coil 36 could be used as a transmitter, and receivers could be provided in known fixed locations). Based upon these transmitted signals a processor can determine the position and orientation of the distal and of the catheter, and translate this determined position into the frame of reference of the imaging system. The position of the distal end of the catheter 22 could also be determined by displacing the distal end of the catheter and determining the position through image processing. The magnet system 34 could be operated to displace the distal end of the catheter. Alternatively, an auxiliary coil 42 could be used to change the magnetic field applied to the distal end of the catheter to displace the catheter. The coil 36 could be energized to change the magnetic moment of the catheter 22 and cause it to move in the applied magnetic field. Once the position of the distal end of the catheter 22 is determined, the processor 28 can display an enhanced indication of the location of the distal end on the display 30. This enhanced indication may be a line indicating the end, such as double lines 44 or a ring corresponding to the distal end which also would help indicate the orientation, or an pointer, such as arrow 46. The enhanced indication can be of increased brightness, distinctive color or it may flash or alternate or change color.

The step of determining the location of the distal end of the medical device can be accomplished in a number of ways, including transmitting signals between at least one reference location and the distal end of the medical device, and more preferably a plurality of reference locations and the distal end of the medical device.

The distal end of the medical device is preferably provided with a receiver having lead wires that extend to the proximal end of the device, where they are connected to the processor that can process the signals received from transmitters at the reference locations can determine the location of the distal tip in the frame of reference of the reference locations. The position of the distal tip can then be transferred to the frame of reference of the imaging system, and an indication of the location of the tip can displayed on x-ray image. This indication can be a highlighted outline of the distal end, a ring or circle to represent the end, an arrow, or some other indication that gives the user a more accurate view of the current position of the distal tip. For example, the contrast on the X-ray image can change from white to black to make the tip of the catheter blink to indicate its position. A positive indication of the tip position is particularly helpful when the medical device contains radiopaque material for delivering into the body. The radiopaque material can obscure the distal end of the device on x-ray images, impairing navigation.

Figure 4:
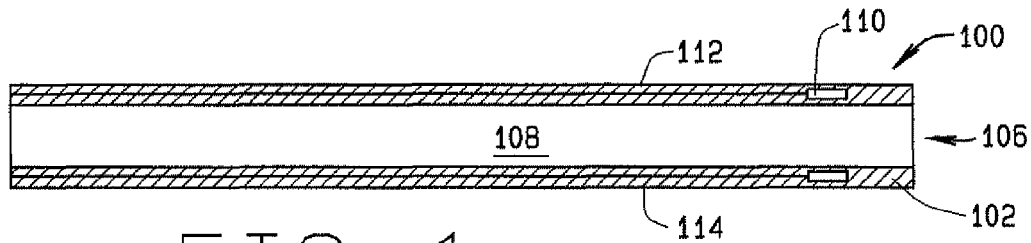
FIG. 4 is a longitudinal cross-sectional view of a catheter incorporating a localization coil in accordance with the principles of this invention.
Figure 5:
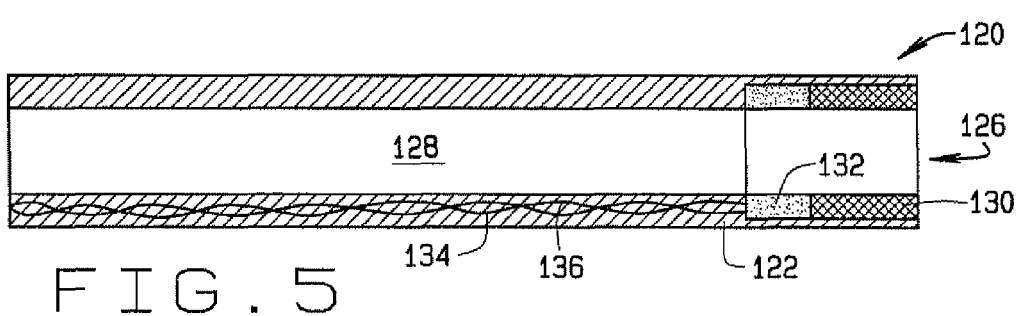
FIG. 5 is a longitudinal cross-sectional view of a magnetically navigable catheter with a localization coil useful in the method of the present invention.

Examples of a conventional catheter and a magnetically navigable catheter adapted for this method are shown in FIGS. 4 and 5. As shown in FIG. 4, a conventional catheter 100 comprises a generally tubular sidewall 102, with a proximal end (not shown), a distal end 106, and a lumen 108 extending therebetween, also has at least one coil 110 adjacent the distal end 106, connected by leads 112 and 114 which extend to the proximal end of the catheter 100. The coil 110 is preferably embedded in the sidewall 102, although it could be secured on the inside or outside of the wall. As shown in FIG. 4, the coil 110 may extend circumferentially around the catheter. Instead of, or in addition to, a circumferentially extending coil, the catheter 100 could have one or more coils in or on the sidewall 102 generally in planes parallel to the axis of the catheter. In some instances it may be preferable to have three mutually perpendicular coils. The coil(s) 110 is preferably made of a radio opaque material (or with other imaging modalities a material that is imaged by such imaging modality so that the distal tip is viewable in the displayed image without the need for a separate marker. Gold and Platinum and alloys of gold or platinum are suitable for this purpose. Alternatively, a radio opaque (or other imagable) marker is provided.

In addition to being used in magnetic localization, the coil(s) 110 can also be used to change the magnetic moment of the distal end of the device to facilitate magnetic navigation of the distal end of the device in a magnetic field applied by an external magnet system, as disclosed in Garibaldi et al., U.S. Pat. No. 6,401,723, issued Jun. 11, 2002, incorporated herein by reference.

As shown in FIG. 5, a magnetically navigable catheter 120 comprises a generally tubular sidewall 122, with a proximal end (not shown), a distal end 126, and a lumen 128 extending therebetween. A tubular magnetically responsive member 130 is embedded in the distal end of the sidewall 122. The magnetically responsive member is preferably made of a permanent magnetic material, such as neodymium-iron-boron or a permeable magnetic material, such as Hiperco, that is of sufficient size and shape to align with an applied magnetic field from an external source magnet (typically about 0.07 to about 0.1 T). At least one coil 132 adjacent the distal end 126, is connected by leads 134 and 136 which extend to the proximal end of the catheter. The coil 132 is preferably embedded in the sidewall 122, proximal to the magnetically responsive element although it could be secured on the inside or outside of the wall. As shown in FIG. 5, the coil 132 may extend circumferentially around the catheter. Instead of, or in addition to, a circumferentially extending coil, the catheter 120 could have one or more coils in or on the sidewall generally in planes parallel to the axis of the catheter. In some instances it may be preferable to have three mutually perpendicular coils. The coil(s) 132 is preferably made of a radio opaque material (or with other imaging modalities a material that is imaged by such imaging modality so that the distal tip is viewable in the displayed image without the need for a separate marker. Gold and Platinum and alloys of gold or platinum are suitable for this purpose. Alternatively, a radio opaque (or other imagable) marker is provided.

In addition to being used in magnetic localization, the coil(s) 132 can also be used to change the magnetic moment of the distal end of the device to facilitate magnetic navigation of the distal end of the device in a magnetic field applied by an external magnet system, as disclosed in Garibaldi et al., U.S. Pat. No. 6,401,723, issued Jun. 11, 2002, incorporated herein by reference.

The coil(s) 110 in the catheter 100, and the coil(s) 132 in the catheter 120, and can act as receivers from signals transmitted from transmitters at fixed reference points, or as transmitters of signals to receivers at the fixed reference points.

In a preferred embodiment of the invention, low frequency magnetic fields are generated in a plurality of coils placed around the patient, as originally proposed by Van Steenwyk, et al in U.S. Pat. No. 4,173,228, and further developed by Acker, et al in U.S. Pat. No. 5,558,091 and others (the disclosures of which are incorporated by reference). The coils are capable of generating magnetic fields of about 1 Gauss or $10^{-4}$ Tesla at the location of the catheter tip, and are typically operated at a plurality of frequencies in the one to ten kiloHertz range. Sensing of the a.c. magnetic field is simply a matter of measuring the voltage induced by the changing applied magnetic field in a small coil near the catheter distal tip. Signals from the individual external coils occur at distinct frequencies and/or at distinct times, and mathematical triangulation-type algorithms are then used to locate the tip relative to the frame of reference of the external coil set. Measured voltages on the order of one milli-Volt are adequate to locate the tip to within a fraction of one millimeter. The voltage induced in the sense coil is given by:

$$V = -\partial\Phi/\partial t = -NA\partial B/\partial t = -2\pi f BNA \quad (1)$$

where
V=voltage induced in the sense coil in volts
f=frequency of applied magnetic field in Hertz
B=amplitude of applied magnetic field in Tesla
NA=turns area product in square m.

For a simple, one layer coil, the turns area product is simply the number of turns in the coil times its cross sectional area. For a multi-layer coil, each layer has its own cross-sectional area, and integrating from the inside to the outside diameter of the coil gives:

$$NA = N_t \pi (d_1^2 + d_1 d_2 + d_2^2)/12 \quad (2)$$

Where
$N_t$=total number of turns in the coil
$d_1$=coil inside diameter
$d_2$=coil outside diameter A worst-case estimate for the total number of turns in the coil assumes that the windings stack on top of one another, and is given by:

$$N_t = L(d_2 - d_1)/(2d_w^2) \quad (3)$$

where
L coil length
$d_w$=wire diameter

Microcatheters which have been developed for drug infusion and repair of vascular defects in the neuro-vasculature are typically less than one mm in outside diameter to facilitate navigation through small blood vessels. These microcatheters have inside diameters up to one-half mm to facilitate optimum delivery volume. Preferred dimensions for a microcatheter embodiment of the present invention are:

$d_1$=0.54 mm
$d_2$=0.92 mm

The length of the coil must be rigid, and forms part of a rigid distal tip. The rigid section of the tip would preferably not be larger than about four mm to facilitate passage into vessel side branches. A preferred embodiment has a magnet at the very distal tip of the microcatheter which is about two mm long. Thus, the worst case coil length is two mm. A small but practical gauge of insulated wire for the coil is AWG#55, having an overall diameter of $d_w$=0.018 mm. Inserting these dimensions into Eq. (3), and then into Eq. (2) gives:

$N_t$~1,200.
NA~500 mm$^2$=5×10$^{-4}$ m$^2$ and evaluating Eq. (1) with a typical frequency of f~4×10$^3$ Hz, and B~10$^{-4}$ Tesla gives a signal voltage amplitude estimate of:

V~10$^{-3}$ Volts=1 milli-Volt, which again is ample signal to locate the catheter tip to within a fraction of one mm.

The receive coil(s) at the tip of the catheter contains a total length of wire equal to the average circumference of the coil times the number of turns, and is equal to nine feet in the preferred embodiment above. If AWG #55 copper wire is used to wind this coil, the resistance will be about 300 Ohms. Gold is much more biocompatible than copper, and is preferred. A gold coil will have a resistance of about 420 Ohms in the preferred embodiment. While the higher resistance will generate more thermal noise for a given input signal, the noise scales as the square root of the resistance and is only about 20% higher for gold than for copper. Gold has another very important advantage over copper. The gold coil is radiopaque, and will mark the position of the coil when X-ray guidance is employed. Without this feature, a gold or platinum marker would be required at the catheter tip, which would further lengthen the stiff part of the tip. The combination radiopaque and location sensing coil enables a visual check on the accuracy of the electromagnetic localization when the coil is visible under fluoroscopy, because an accurate electromagnetic location mark should fall on top of the radiopaque tip when displayed on the X-ray monitor. Conventional guidance using X-ray fluoroscopy can be employed until the tip becomes obscured by other radiopaque materials, after which electromagnetic localization can be employed. In short, there are advantages to having a bi-modal localization capability in the tip coil. While platinum is a more conventional radiopaque marker material, a platinum coil in the preferred embodiment would have a resistance of about 1,900 Ohms, and would generate about 250% more thermal noise than the copper coil for a given input signal. Thus, a gold coil is preferred material.

Of course, the distal end of the medical device could be provided with a transmitter, that transmits to receivers at the reference locations, or multiple transmitters or multiple receivers can be provided on the medical device.

In the case of a radio opaque transmitter or receiver on the medical device, the enhanced indication of the distal tip may be an indication of the location of this coil, thus the user "sees" the coil on images, and where there is interference the method of the invention provides an enhanced display of the location of the coil, so the user has the same reference point, regardless of whether the coil can actually be seen in the image.

Other methods of localizing the distal end of the medical device can be used, such as ultrasound or electric-potential.

The step of determining the location of the distal end of the medical device can also be accomplished by displacing the distal end of the device slightly, and through processing the images before and after the displacement determining the position of the distal end of the medical device. This allows the position of the distal end to be determined in the frame of reference of the x-ray image, so that the position of the distal tip of the medical device can be readily indicated on the display. In the case of a conventionally navigated medical device, the displacement can be by rotating the proximal end, by advancing an/or retracting the proximal end, or by manipulating the tip with push wires or pull wires. In the case of non-conventionally navigated device, the distal tip can be displaced by operating an electrostrictive or magnetostrictive element.

Figure 6:
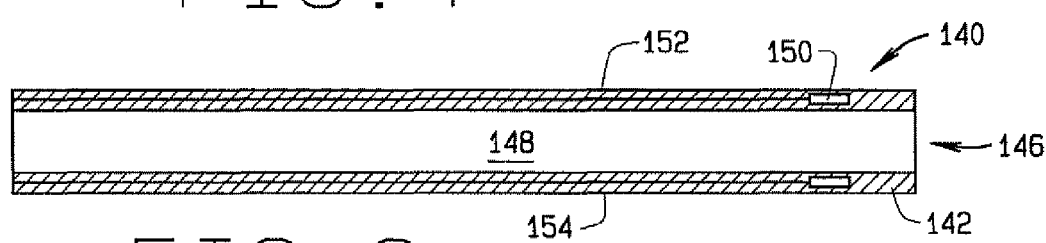
FIG. 6 is a longitudinal cross-sectional view of a catheter incorporating a displacement coil useful in the method of the present invention.
Figure 7:
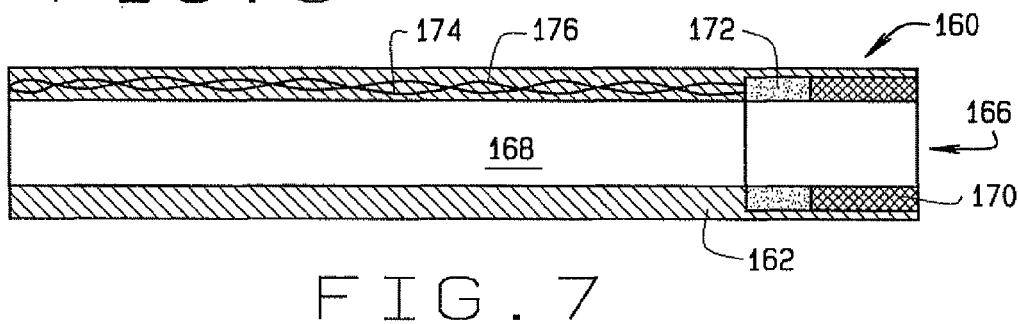
FIG. 7 is a longitudinal cross-sectional view of a magnetically navigable catheter with a displacement coil useful in the method of the present invention.

Examples of a conventional catheter and a magnetically navigable catheter adapted for this method are shown in FIGS. 6 and 7. As shown in FIG. 6, a conventional catheter 140 comprises a generally tubular sidewall 142, with a proximal end (not shown), a distal end 146, and a lumen 148 extending therebetween, also has at least one coil 150 adjacent the distal end 146, connected by leads 152 and 154 which extend to the proximal end of the catheter. The coil 150 is preferably embedded in the sidewall 62, although it could be secured on the inside or outside of the wall. As shown in FIG. 6, the coil 150 may extend circumferentially around the catheter 140. Instead of, or in addition to, a circumferentially extending coil, the catheter 140 could have one or more coils in or on the sidewall generally in planes parallel to the axis of the catheter. In some instances it may be preferable to have three mutually perpendicular coils. The coil 150 is preferably made of a radio opaque material (or with other imaging modalities a material that is imaged by such imaging modality so that the distal tip is viewable in the displayed image without the need for a separate marker. Gold and Platinum and alloys of gold or platinum are suitable for this purpose. Alternatively, a radio opaque (or other imagable) marker is provided.

In addition to being used in displacing the distal end of the catheter 140, the coil(s) 150 can also be used to change the magnetic moment of the distal end of the device to facilitate magnetic navigation of the distal end of the device in a magnetic field applied by an external magnet system, as disclosed in Garibaldi et al., U.S. Pat. No. 6,401,723, issued Jun. 11, 2002, incorporated herein by reference.

As shown in FIG. 7, a magnetically navigable catheter 160 comprises a generally tubular sidewall 162, with a proximal end (not shown), a distal end 166, and a lumen 168 extending therebetween. A tubular magnetically responsive member 170 is embedded in the distal end of the sidewall 162. The magnetically responsive member is preferably made of a permanent magnetic material, such as neodymium-iron-boron or a permeable magnetic material, such as Hiperco, that is of sufficient size and shape to align with an applied magnetic field from an external source magnet. At least one coil 172 adjacent the distal end 166, connected by leads 174 and 176 which extend to the proximal end of the catheter. The coil 172 is preferably embedded in the sidewall 162, proximal to the magnet although it could be secured on the inside or outside of the wall. As shown in FIG. 7, the coil 172 may extend circumferentially around the catheter 160. Instead of, or in addition to, a circumferentially extending coil, the catheter 160 could have one or more coils in or on the sidewall generally in planes parallel to the axis of the catheter. In some instances it may be preferable to have three mutually perpendicular coils.

The coil 172 is preferably made of a radio opaque material (or with other imaging modalities a material that is imaged by such imaging modality so that the distal tip is viewable in the displayed image without the need for a separate marker. Gold and Platinum and alloys of gold or platinum are suitable for this purpose. Alternatively, a radio opaque (or other imagable) marker is provided.

In addition to being used in displacing the distal end of the catheter 160, the coil(s) 172 can also be used to change the magnetic moment of the distal end of the device to facilitate magnetic navigation of the distal end of the device in a magnetic field applied by an external magnet system, as disclosed in Garibaldi et al., U.S. Pat. No. 6,401,723, issued Jun. 11, 2002, incorporated herein by reference.

The coil(s) 150 in the catheter 140, and the coil(s) 172 in the catheter 160, and can be selectively connected to a source of electric power to change the magnetic moment of the distal end of the catheter, thereby temporarily displacing the distal end of the catheter so that the location of the distal end of the catheter can be located by signal processing.

In the case of a magnetically navigated medical device, in which the medical device has a magnetically responsive element for aligning with an applied magnetic field the displacement of the distal tip can be effected by changing the direction or intensity of the applied magnetic fields from the external source magnet. An auxiliary magnet can also be provided outside the body to change the position of the distal end of the medical device. This auxiliary magnet could be a permanent magnet, but is preferably an electromagnet so that the field can be turned on and off. An auxiliary coil could alternatively be provided on the medical device, to temporarily change the magnetic moment of the medical device to displace the medical device within the magnetic field of the external source magnets.

Figure 8:
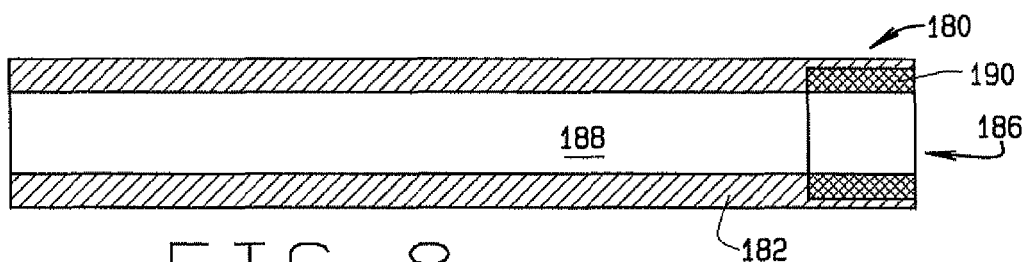
FIG. 8 is a longitudinal cross-sectional view of a magnetically navigable catheter useful in the method of the present invention.

As shown in FIG. 8, a magnetically navigable catheter 180 comprises a generally tubular sidewall 182, with a proximal end (not shown), a distal end 186, and a lumen 188 extending therebetween. A tubular magnetically responsive member 190 is embedded in the distal end of the sidewall 182. The magnetically responsive member is preferably made of a permanent magnetic material, such as neodymium-iron-boron or a permeable magnetic material, such as Hiperco, that is of sufficient size and shape to align with an applied magnetic field from an external source magnet. The distal tip of catheter 80 responds to changes in the applied magnetic field and can be displaced by changing the magnetic field being applied by the external source magnet, or by temporarily using an auxiliary or boost magnet to displace the distal tip. A radio opaque marker could be provided to facilitate viewing the distal tip on x-ray images.

The method of the present invention is particularly useful for navigating medical devices that deliver radiopaque materials, such as flowable, settable embolic materials, or embolizing coils. In these cases the radiopaque material inside the medical device can make it difficult to accurately locate the distal end of the device in an x-ray image. It can be even more difficult after radiopaque material has been ejected from the medical device into the operating region. Thus, for example, in navigating the distal end of a catheter to the site of a vascular defect, such as an aneurysm, the user may not be able to accurately identify the distal end of the catheter, impairing navigation. Once radiopaque material (e.g., a flowable, settable embolic material or embolizing coils) has been ejected from the catheter, it can even more difficult to identify the distal end of the catheter to complete the procedure. The present invention solves this difficulty by accurately locating the tip, and indicating the position of the tip on the displayed x-ray image of the operating region. The user can then determine how best to position the distal tip to complete the procedures.

What is claimed is:

1. A medical device and system for navigating the medical device through an operating region in a subject's body, comprising:

a plurality of transmitting devices at known fixed locations relative to the subject's body, being configured to transmit signals from fixed reference locations;

a medical device having a plurality of lead wires that extend through the length of the medical device and connect to at least three coils in the distal end portion of the medical device, the at least three coils comprising a radiopaque material and being capable of receiving the signals transmitted from the plurality of transmitters and of generating magnetic fields of at least about 1 Gauss at the location of the distal end portion of the medical device to thereby establish a magnetic moment at the distal end portion;

a processor in connection with the plurality of lead wires, the processor being configured to process the signals received from the transmitters by the at least three coils and to determine the location of the distal tip relative to the frame of reference of the reference locations;

an external source magnet for applying a magnetic field to the operating region of the subject's body, the external source magnet being configured to change the direction of the applied magnetic field;

an X-ray imaging system capable of identifying the position of the at least three radiopaque coils relative to markers positioned at known reference locations, to thereby determine the position of the distal end portion for facilitating navigation of the medical device;

a power source that may be selectively connected to one or more of the at least three coils to establish a magnetic moment in the distal end portion of the medical device, which magnetic moment causes the distal end of the medical device to orient relative to the applied magnetic field, to thereby direct the distal end portion of the medical device;

wherein when the distal end portion of the medical device is being navigated in the presence of a flowable radiopaque material in the subject's body that impairs the accurate location of the radiopaque coils via the X-ray imaging system, the system is configured to selectively connect electric power to one or more of the three coils to change the magnetic moment relative to an externally applied magnetic field, to cause the temporary displacement of the distal end portion so that the location of the distal end portion can be located by the processor that receives signals, to thereby determine the location of the distal end portion within the flowable radiopaque material.

2. The system of claim 1, wherein the at least three coils are made of an electrically conductive gold metal that has a resistance equal to or less that about 420 Ohms.

3. The system of claim 1, further comprising a magnetically responsive member disposed on the distal end portion of the medical device, wherein when the direction or intensity of the magnetic field applied by the external source magnet is changed, the magnetically responsive member and the magnetic moment established by the electrically powered coils cause the distal end portion of the medical device to orient relative to the magnetic field, to thereby direct the distal end portion for navigating the medical device.

4. The system of claim 3, wherein when the distal end portion of the medical device is being navigated in the presence of a flowable radiopaque material in the subject's body that impairs the accurate location of the radiopaque coils via the X-ray imaging system, the system is configured to selectively connect electric power to one or more of the three coils to change the magnetic moment relative to the externally applied magnetic field, such that the magnetically responsive element and the magnetic moment cause the temporary displacement of the distal end so that the location of the distal end portion can be located by the processor that receives signals, to thereby determine the location of the distal end portion within the flowable radiopaque material.

5. The system of claim 4, wherein the at least three coils are made of an electrically conductive gold metal that has a resistance equal to or less that about 420 Ohms.

6. A method of navigating the distal end of a medical device through an operating region in a subject's body, comprising:
introducing into a subject's body a medical device having a plurality of lead wires that extend through the length of the medical device and connect to at least three coils made of a radiopaque material that are disposed in the distal end portion of the medical device and are capable of receiving transmitted signals;
transmitting signals from a plurality of transmitting devices at known fixed locations relative to the subject's body, to provide one or more signals transmitted from fixed reference locations that are received by the at least three coils in the medical device;
processing the signals received from the transmitters by the at least three coils to determine the location of the distal tip relative to the frame of reference of the reference locations;
applying a magnetic field of a select intensity and direction to the operating region of the subject's body using an external source magnet;
using an X-ray imaging system to identify the position of the at least three radiopaque coils relative to markers positioned at known reference locations, to thereby determine the position of the distal end portion for facilitating navigation of the medical device;
selectively connecting an electrical power source to one or more of the at least three coils to establish a magnetic moment of at least 1 Gauss or 0.0004 Tesla in the distal end portion of the medical device, which magnetic moment causes the distal end of the medical device to orient relative to the applied magnetic field, to thereby direct the distal end portion of the medical device; and
selectively connecting electric power to one or more of the three coils when the distal end portion of the medical device is being navigated in the presence of a flowable radiopaque material that impairs the accurate identification of the radiopaque coils using the X-ray imaging system, where the selective connection of electrical power to one or more coils changes the magnetic moment relative to the externally applied magnetic field, such that the magnetic moment established by the electrically powered coils cause the temporary displacement of the distal end portion so that the distal end portion can be located by the processing step for processing signals to determine the location of the distal end portion within the flowable radiopaque material.

7. The method of claim 6 further comprising the step of providing an indication of the position of the distal end portion on a displayed X-ray image of the operating region.

8. The method of claim 7, wherein the step of processing the signals comprises a processor in connection with the plurality of lead wires, which is configured to process the signals received from the transmitters by the at least three coils and to determine the location of the distal tip relative to the frame of reference of the reference locations.

9. A method of navigating the distal end of a medical device through an operating region in a subject's body, comprising:
introducing into a subject's body a medical device having at least one magnetically responsive element thereon, and a plurality of lead wires that extend through the length of the medical device and connect to at least three coils made of a radiopaque material which are capable of receiving transmitted signals, the at least three coils and magnetically responsive element being disposed at the distal end portion of the medical device;
transmitting signals from a plurality of transmitting devices at known fixed locations relative to the subject's body, to provide one or more signals transmitted from fixed reference locations that are received by the at least three coils in the medical device;
processing the signals received from the transmitters by the at least three coils to determine the location of the distal tip relative to the frame of reference of the reference locations;
using an X-ray imaging system to identify the position of the at least three radiopaque coils relative to markers positioned at known reference locations, to thereby determine the position of the distal end portion for facilitating navigation of the medical device;
selectively connecting an electrical power source to one or more of the at least three coils to generate a magnetic field of at least about 1 Gauss or about 0.0004 Tesla at the location of the distal end portion of the medical device, to thereby establish a magnetic moment at the distal end portion;
applying a magnetic field of a select intensity and direction to the operating region of the subject's body using an external source magnet, such that the magnetically responsive member and the magnetic moment established by the electrically powered coils cause the distal end portion of the medical device to orient relative to the magnetic field, to thereby direct the distal end portion for navigating the medical device; and selectively connecting electric power to one or more of the three coils when the distal end portion of the medical device is being navigated in the presence of a flowable radiopaque material that impairs the accurate identification of the radiopaque coils using the X-ray imaging system, where the selective connection of electrical power to one or more coils changes the magnetic moment relative to the externally applied magnetic field, such that the magnetically responsive member and the magnetic moment established by the electrically powered coils cause the temporary displacement of the distal end portion so that the distal end portion can be located by the processing step for processing signals to determine the location of the distal end portion within the flowable radiopaque material.

10. The method of claim 9 further comprising the step of providing an indication of the position of the distal end portion on a displayed X-ray image of the operating region.

11. The method of claim 10, wherein the step of processing the signals comprises a processor in connection with the plurality of lead wires, which is configured to process the signals received from the transmitters by the at least three coils and to determine the location of the distal tip relative to the frame of reference of the reference locations.

* * * * *